United States Patent [19]

Fuchs et al.

[11] Patent Number: 4,491,585
[45] Date of Patent: Jan. 1, 1985

[54] COMBATING PESTS WITH NOVEL PHENOXYPYRIDYLMETHYL ESTERS

[75] Inventors: Rainer Fuchs, Wuppertal; Ingeborg Hammann, Cologne; Bernhard Homeyer, Leverkusen; Wilhelm Stendel, Wuppertal, all of Fed. Rep. of Germany

[73] Assignee: Bayer Aktiengesellschaft, Leverkusen, Fed. Rep. of Germany

[21] Appl. No.: 355,044

[22] Filed: Mar. 5, 1982

[30] Foreign Application Priority Data

Mar. 25, 1981 [DE] Fed. Rep. of Germany ....... 3111644

[51] Int. Cl.³ .................... C07D 213/64; A01N 43/40
[52] U.S. Cl. .................................. 424/263; 546/302; 546/301; 549/429
[58] Field of Search ................ 546/302, 301; 424/263; 542/429

[56] References Cited

U.S. PATENT DOCUMENTS 4,163,787  8/1979  Malhotra et al. .............. 424/263
4,183,942  1/1980  Engel ........................... 424/274
4,285,954  8/1981  Brown et al. .................. 424/263

FOREIGN PATENT DOCUMENTS 0037851  10/1981  Fed. Rep. of Germany ...... 424/263
2079282   1/1982  United Kingdom ............... 424/263

Primary Examiner—Henry R. Jiles
Assistant Examiner—Robert C. Whittenbaugh
Attorney, Agent, or Firm—Sprung, Horn, Kramer & Woods

[57] ABSTRACT

New phenoxypyridylmethyl esters of the general formula

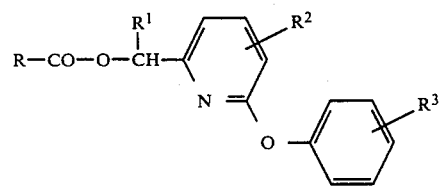

wherein $R^1$, $R^2$ and $R^3$ have the meaning given in the description and
R represents the radical

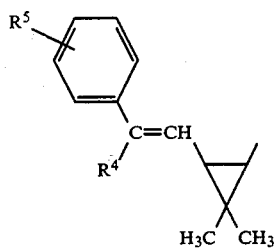

wherein $R^4$ and $R^5$ have the meaning given in the description, and represents the radical

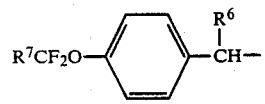

wherein $R^6$ and $R^7$ have the meaning given in the description, are obtained by a process in which carboxylic acids of the general formula

R—COOH   (II)

wherein R has the meaning given previously, or reactive derivatives of these acids, are reacted with phenoxypyridyl alcohols of the general formula

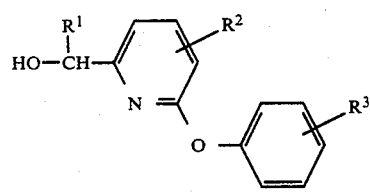

wherein $R^1$, $R^2$ and $R^3$ have the meaning given above, or with reactive derivatives of these alcohols, if appropriate in the presence of acid acceptors, if appropriate in the presence of catalysts and if appropriate in the presence of diluents. The new phenoxypyridylmethyl esters of the formula (I) are distinguished by a high pesticidal, particularly insecticidal and acardicidal activity.

9 Claims, No Drawings

COMBATING PESTS WITH NOVEL PHENOXYPYRIDYLMETHYL ESTERS

The invention relates to certain new phenoxypyridylmethyl esters, to a process for their production and to their use as agents for combating pests, especially as insecticides and acaricides.

It is known that certain carboxylic acid esters, such as 3-phenoxy-benzyl 3-(2-chloro-2-phenyl-vinyl)-2,2-dimethyl-cyclopropanecarboxylate and 6-phenoxy-2-pyridyl-methyl 3-(2,2-dichloro-vinyl)-2,2-dimethyl-cyclopropane-carboxylate, have insecticidal and acaricidal properties (see U.S. Pat. Nos. 4,183,942 and 4,163,787). However, the action of these compounds is not always satisfactory, particularly for low active compound concentrations and use quantities.

The present invention now provides, as new compounds, the phenoxypyridylmethyl esters of the general formula

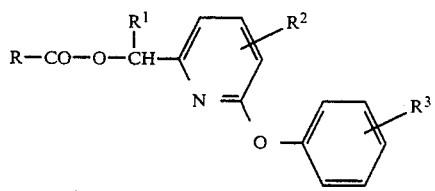

wherein R represents a radical of the general formula

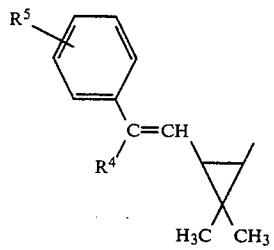

wherein
- $R^4$ represents a hydrogen, chlorine or bromine atom, a cyano group or an optionally halogen-substituted alkyl group and
- $R^5$ represents a hydrogen or halogen atom or an optionally halogen-substituted alkyl or alkoxy group, or
- R also represents a radical of the general formula

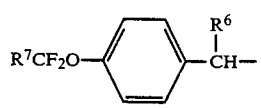

wherein
- $R^6$ represents an isopropyl or cyclopropyl group and
- $R^7$ represents a hydrogen or fluorine atom or a trifluoromethyl or chloro-(di)fluoromethyl group,
- $R^1$ represents a hydrogen atom, or a cyano, alkyl, alkenyl, or alkinyl group; the alkyl, alkenyl and alkinyl groups containing up to 4 carbon atoms and optionally being substituted by halogen, and
- $R^2$ and $R^3$ are identical or different and represent a hydrogen or halogen atom.

The general formula (I) includes the various possible stereoisomers and optical isomers, as well as mixtures thereof.

According to the present invention we further provide a process for the production of a compound of the present invention characterized in that a carboxylic acid of the general formula

wherein R has the meaning given above, or a reactive derivative thereof, is reacted with a phenoxypyridyl alcohol of the general formula

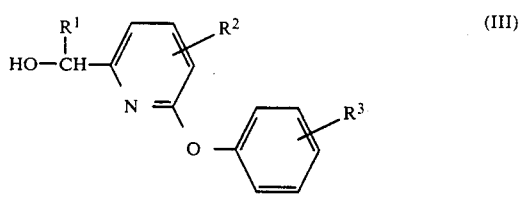

wherein $R^1$, $R^2$ and $R^3$ have the meanings given above, or with a reactive derivative thereof, if appropriate in the presence of an acid acceptor, if appropriate in the presence of a catalyst and if appropriate in the presence of a diluent.

The new phenoxypyridylmethyl esters of the present invention are distinguished by a high pesticidal, particularly insecticidal and acaricidal, activity.

Surprisingly, the compounds of the formula (I) according to the invention exhibit a considerably more powerful insecticidal and acaricidal action than the compounds which are known from the state of the art and which are of analogous constitution and identical direction of action.

Preferred compounds of the present invention are those
wherein R represents a radical of the general formula

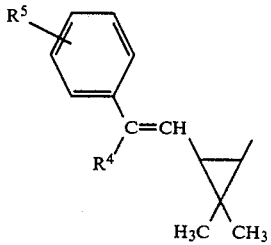

wherein
- $R^4$ represents a hydrogen, chlorine or bromine atom, a cyano group or a $C_1$ to $C_4$ alkyl group which is optionally substituted by fluorine or chlorine, and
- $R^5$ represents a hydrogen, chlorine, or bromine atom or an optionally fluorine-substituted and/or chlorine-substituted $C_1$ to $C_4$ alkyl or $C_1$ to $C_4$ alkoxy group, or R also represents a radical of the general formula

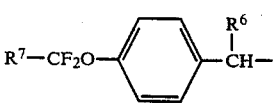

wherein $R^6$ represents an isopropyl or cyclopropyl group and
$R^7$ represents a hydrogen or fluorine atom or a trifluoromethyl or chloro-(di)fluoromethyl group,
$R^1$ represents a hydrogen atom or a cyano, methyl, ethyl, propyl, ethenyl, propenyl, ethinyl or propinyl group, and
$R^2$ and $R^3$ represent a hydrogen, fluorine, chlorine or bromine atom.

Particularly preferred compounds of the present invention are those
wherein R represents a radical of the general formula

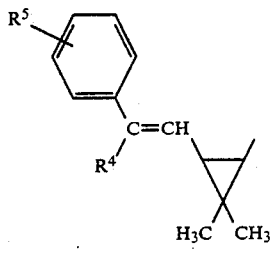

wherein
$R^4$ represents a chlorine atom and
$R^5$ represents a hydrogen atom or a chloride atom (in the para-position), or
R also represents a radical of the general formula

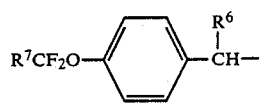

wherein
$R^6$ represents an isopropyl group and
$R^7$ represents a fluorine atom,
$R^1$ represents a hydrogen atom or a cyano group, and
$R^2$ and $R^3$ represent hydrogen atoms.

In a preferred reaction variant (a) of the process according to the present invention a carboxylic acid-chloride of the general formula $$R-CO-Cl \qquad (II\ a)$$

wherein R has the meaning given above,
is reacted with a phenoxypyridyl alcohol of the formula (III), as defined above, in the presence of an acid acceptor and a diluent.

In a further preferred reaction variant (b) of the process according to the invention, compounds of the formula (I) wherein $R^1$ represents a cyano group are prepared by reacting a carboxylic acid-chloride of the formula (II a), as defined above, with a phenoxypyridinecarbaldehyde (pheoxy-formyl-pyridines) of the general formula

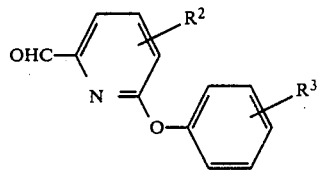

wherein $R^2$ and $R^3$ have the meaning given above, and at least an equimolar quantity of an alkali metal cyanide (i.e. sodium cyanide or potassium cyanide), in the presence of water and of a water-immiscible organic solvent and, if necessary, in the presence of a catalyst.

If, for example, 3-(2-chloro-2-phenyl-vinyl)-2,2-dimethyl-cyclopropanecarboxylic acid-chloride and 6-phenoxy-2-pyridyl-methanol are used as the starting materials in process variant (a), and 3-methyl-2-(4-difluoromethoxyphenyl)-butanoic acid-chloride, sodium cyanide and 6-phenoxy-pyridine-2-carbaldehyde are used as the starting materials in variant (b), the reactions proceeding in the two process variants can be represented by the following equations:

(a)

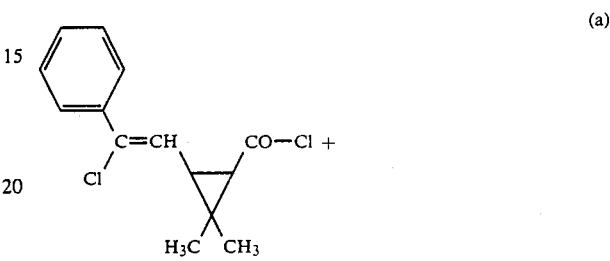

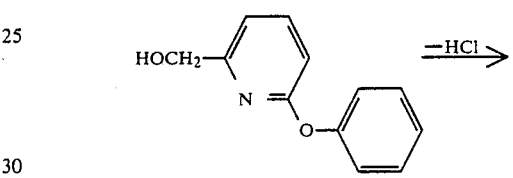

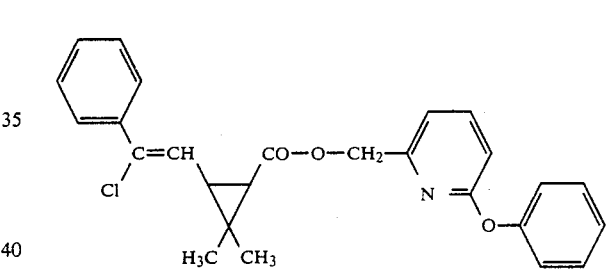

(b)

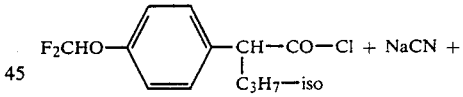

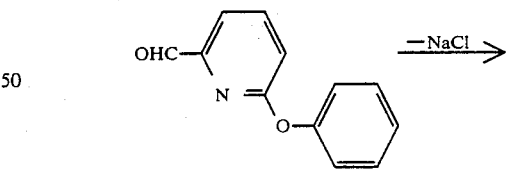

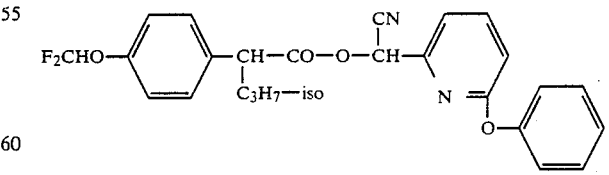

Preferred carboxylic acids of formula (II) and corresponding acid-chlorides of formula (II a) to be used as starting materials in the process of the present invention are those in which R has the same meaning as given in the definition of preferred or particularly preferred compounds of the present invention.

The following may be mentioned as examples of the compounds of the formula (II a): 3-(2-chloro-2-phenyl-vinyl)- and 3-(2-chloro-2-(4-chloro-phenyl)-vinyl)-2,2-dimethyl-cyclopropanecarboxylic acid-chloride, and 2-(4-trifluoromethoxyphenyl)- and 2-(4-difluoromethoxy-phenyl)-3-methyl-butanoic acid-chloride.

Compounds of the formulae (II) and (II a) are known (see U.S. Pat. Nos. 4,183,942 and 4,199,595).

Preferred phenoxypyridyl alcohols of formula (III) to be used as starting materials in the process of the present invention are those in which $R^1$, $R^2$ and $R^3$ represent those radicals which have already been mentioned in the definition of preferred or particularly preferred compounds of the present invention.

The following may be mentioned as examples of the starting compounds of the formula (III): 6-phenoxy-2-pyridylmethanol and 6-phenoxy-2-pyridyl-α-cyano-methanol.

The compounds of the formula (III) are already known (see U.S. Pat. No. 4,163,787).

Preferred phenoxypyridinecarbaldehydes of formula (IV) to be used as the starting materials in reaction variant (b) according to the present invention are those in which $R^2$ and $R^3$ have the meanings given in the definition of the preferred and particularly preferred compounds of the present invention.

6-Phenoxy-pyridine-2-carbaldehyde may be mentioned as an example of phenoxypyridinecarbaldehydes of formula (IV).

The compounds of the formula (IV) are also known (see U.S. Pat. No. 4,163,787).

The process for the preparation of the new compounds of the formula (I) is preferably carried out using diluents, in all reaction variants. Virtually any of the inert organic solvents are suitable diluents. These include, in particular, aliphatic and aromatic, optionally halogenated hydrocarbons (such as pentane, hexane, heptane, cyclohexane, petroleum ether, benzine, ligroin, benzene, toluene, xylene, methylene chloride, ethylene chloride, chloroform, carbon terachloride, chlorobenzene and o-dichlorobenzene), ethers (such as diethyl ether, dibutyl ether, glycol dimethyl ether, diglycol dimethyl ether, tetrahydrofuran and dioxane), ketones (such as acetone, methyl ethyl ketone, methyl isopropyl ketone and methyl isobutyl ketone), esters (such as methyl acetate and ethyl acetate), nitriles (such as acetonitrile and propionitrile), amides (such as dimethylformamide, dimethylacetamide and N-methylpyrrolidone), and dimethylsulphoxide, tetramethylenesulphone and hexamethylphosphoric acid triamide.

Reaction variant (a) of the process according to the present invention is preferably carried out in the presence of acid acceptors. Any of the customary acid-binding agents can be used as the acid acceptors. Alkali metal carbonates and alcoholates (such as sodium and potassium carbonate, sodium and potassium methylate or ethylate) and also aliphatic, aromatic or heterocyclic amines (for example triethylamine, trimethylamine, dimethylaniline, dimethylbenzylamine, pyridine, diazabicyclooctane, diazabicyclononene and diazabicycloundecene), have proved particularly suitable.

Reaction variant (b) of the process according to the invention is carried out in the presence of water and of one of the abovementioned organic solvents, provided that it is not miscible with water. The abovementioned hydrocarbons are particularly suitable for this purpose.

Compounds which are suitable fo the transfer of anions from water into organic solvents are preferably used as catalysts in reaction variant (b). Benzyl-triethyl-ammonium hydrogen sulphate, tetrabutylammonium bromide and methyl-trioctyl-ammonium chloride ("Aliquat" 336—Trade Mark) are examples of these compounds.

In all process variants, the reaction temperature can be varied within a relatively wide range. In general, the reaction is carried out at a temperature between 0° and 100° C., preferably at a temperature between 10° and 50° C.

The process according to the invention is carried out, in general, under normal pressure. The starting materials are customarily employed in equimolar quantities for carrying out the process according to the invention. An excess of either of the reaction components has no substantial advantages. The starting materials are combined in suitable diluents and, if appropriate after the addition of an acid acceptor and/or a catalyst, are stirred until the end of the reaction.

The working-up can be carried out according to customary methods, for example by diluting the reaction mixture, if appropriate, with water and/or a water-immiscible organic solvent, such as toluene, separating off the organic phase, washing it with water, drying it and filtering it, and carefully distilling off the solvent from the filtrate, under reduced pressure and at a moderately elevated temperature ("incipient distillation").

The active compounds are well tolerated by plants, have a favorable level of toxicity to warm-blooded animals, and are suitable for combating arthropod pests, especially insects and arachnida, which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and *Scutigera spec.;* from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus, Gryllotalpa spp., Locusta migratoria migratorioides, Melanoplus differentialis* and *Schistocerca gregaria;* from the order of the Dermaptera, for example *Forficula auricularia;* from the order of the Isoptera, for example *Reticulitermes spp.;* from the order of the Anoplura, for example *Phylloxera vastatrix, Pemphigus spp., Pediculus humanus corporis, Haematopinus spp.* and *Linognathus spp.;* from the order of the Mallophaga, for example *Trichodectes spp.* and *Damalinea spp.;* from the order of the Thysanoptera, for example *Hercinothrips femoralis* and *Thrips tabaci;* from the order of the Heteroptera, for example *Eurygaster spp., Dysdercus intermedius, Piesma quadrata, Cimex lectularius, Rhodnius prolixus* and *Triatoma spp.;* from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus spp., Phorodon humuli, Rhopalosiphum padi, Empoasca spp., Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus spp.* and *Psylla spp.;* from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria spp., Bucculatrix thurberiella, Phyllocnistis citrella, Agrotis spp., Euxoa spp., Feltia spp., Earias insulana, Heliothis spp., Laphygma exigua, Mamestra brassicae, Panolis flammea, Prodenia litura, Spodoptera spp., Trichoplusia ni, Carpocapsa pomonella, Pieris spp., Chilo spp., Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica spp., Psylliodes chrysocephala, Epilachna varivestis, Atomaria spp., Oryzaephilus surinamensis, Anthonomus spp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Conoderus spp., Melolontha melolontha, Amphimallon solstitialis* and *Costelytra zealandica;* from the order of the Hymenoptera, for example *Diprion spp., Hoplocampa spp., Lasius spp., Monomorium pharaonis* and *Vespa spp.;* from the order of the Diptera, for example *Aedes spp., Anopheles spp., Culex spp., Drosophila melanogaster, Musca spp., Fannia spp., Calliphora erythrocephala, Lucilia spp., Chrysomyia spp., Cuterebra spp., Gastrophilus spp., Hyppobosca spp., Stomoxys spp., Oestrus spp., Hypoderma spp., Tabanus spp., Tannia spp., Bibio hortulanus, Oscinella frit, Phorbia spp., Pegomyia hyoscyami, Ceratitis capitata, Dacus olea* and *Tipula paludosa;* from the order of the Siphonaptera, for example *Xenopsylla cheopis* and *Ceratophyllus spp.;* from the class of the Arachnida, for example *Scorpio maurus* and *Latrodectus mactans;* from the order of the Acarina, for example *Acarus siro, Argas spp., Ornithodoros spp., Dermanyssus gallinae, Eriophyes ribis, Phyllocoptruta oleivora, Boophilus spp., Rhipicephalus spp., Amblyomma spp., Hyalomma spp., Ixodes spp., Psoroptes spp., Chorioptes spp., Sarcoptes spp., Tarsonemus spp., Bryobia praetiosa, Panonychus spp.* and *Tetranychus spp..*

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons phenylureas and substances produced by microorganisms.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 100% by weight of active compound, preferably between 0.0001 and 1% by weight.

The compounds are employed in a customary manner appropriate for the use forms.

When used against pests harmful to health and pests of stored products, the active compounds are distinguished by an excellent residual action on wood and clay as well as a good stability to alkali or limed substrates.

The active compounds according to the invention are also suitable for combating ectoparasites and endoparasites in the field of veterinary medicine.

The present invention also provides pesticidal composition containing as active ingredient a compound of the present invention in admixture with a solid or liquefied gaseous diluent or carrier or in admixture with a liquid diluent or carrier containing a surface-active agent.

The present invention also provides a method of combating pest (in particular arthropods, especially insects or acarids) which comprises applying to the pests, or to a habitat thereof, a compound of the present invention alone or in the form of a composition containing as active ingredient a compound of the present invention in admixture with a diluent or carrier.

The present invention also provides a method of freeing or protecting domesticated animals from parasites which comprises applying to said animals a compound according to the present invention, in admixture with a diluent or carrier.

The present invention further provides crops protected from damage by pests by being grown in areas in which immediately prior to and/or during the time of the growing a compound of the present invention was applied alone or in admixture with a diluent or carrier.

It will be seen that the usual methods of providing a harvested crop may be improved by the present invention.

The present invention further provides domesticated animals whenever freed or protected from parasites by the application to said animals of a compound according to the present invention, in admixture with a diluent or carrier.

The active compounds according to the invention may be used in a known manner in the veterinary sector, such as by oral administration, for example in the form of tablets, capsules, drinks and granules, by dermal application, for example by means of dipping, spraying, pouring on, spotting on, and dusting, and by parenteral administration, for example by means of an injection.

PREPARATIVE EXAMPLES

Example 1

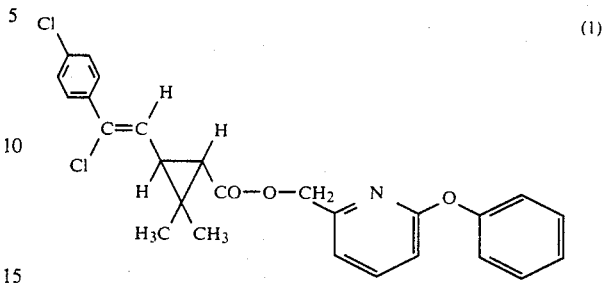

(1)

4.02 g (0.02 mol) of (6-phenoxy-2-pyridinyl)-methanol and 6.07 g (0.02 mol) of (±)-trans-Z-3-(2-chloro-2-(4-chloro-phenyl)-vinyl)-2,2-dimethyl-1-cyclopropanecarboxylic acid-chloride were dissolved in 100 ml of anhydrous toluene, and 2 g of pyridine, dissolved in 10 ml of anhydrous toluene, were added dropwise to the solution at 20°–25° C., while stirring. The mixture was then stirred for a further 3 hours at 25° C. The reaction mixture was poured into 150 ml of water, and the organic phase was separated off and again washed with 100 ml of water. The toluene phase was then dried over sodium sulphate and the solvent was distilled off in a water jet vacuum. The last solvent residues were removed by incipient distillation for a short time at a bath temperature of 60° C./1 mm Hg. 8.6 g (92% of theory) of (6-phenoxy-2-pyridinyl)-methyl (±)-trans-Z-3-(2-chloro-2-(4-chlorophenyl)-vinyl)-2,2-dimethyl-1-cyclopropanecarboxylate were obtained as a yellow viscous oil. The structure was established by the $^1$H-NMR spectrum.

| $^1$H—NMR in CDCl$_3$/TMSτ(ppm): | |
|---|---|
| aromatic-H: | 2.2–3.4 (m/12 H) |
| vinyl-H: | 4.15 (s/1 H) |
| benzyl-H: | 4.88 (s/2 H) |
| cyclopropane-H: | 7.28–7.58 (m/1 H) |
| cyclopropane-H: | 8.17 (d/1 H) |
| dimethyl-H: | 8.6 (s/3 H) |
| dimethyl-H: | 8.74 (s/3 H) |

Example 2

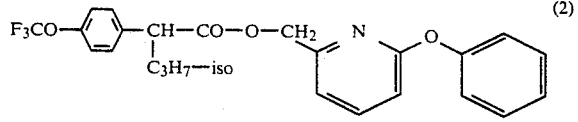

(2)

4.02 g (0.02 mol) of (6-phenoxy-2-pyridinyl)-methanol and 5.6 g (0.02 mol) of α-isopropyl-4-trifluoro-methoxyphenyl-acetic acid-chloride were dissolved in 100 ml of anhydrous toluene, and 2 g of pyridine, dissolved in 20 ml of anhydrous toluene, were added dropwise to the solution at 20° to 25° C., while stirring. The mixture was then stirred for a further 3 hours at 25° C. The reaction mixture was poured into 150 ml of water, and the organic phase was separated off and again washed with 100 ml of water. The toluene phase was then dried over sodium sulphate and the solvent was distilled off in a water jet vacuum. The last solvent residues were removed by incipient distillation for a short time at a bath temperature of 60° C./1 mm Hg. 7.6 g (85.4% of theory) of (6-phenoxy-2-pyridinyl)-methyl α-isopropyl-4-trifluoromethyl-phenylacetate were obtained as a yellow viscous oil. The structure was established by the ¹H-NMR.

| ¹H—NMR in CDCl₃/TMS τ(ppm): | |
|---|---|
| aromatic-H: | 2.32–3.38 (m/8 H) |
| benzyl-H: | 4.9 (s/2 H) |
|  | 6.71 (d/1 H) |
|  | 7.43–7.81 (m/1 H) |
| dimethyl-H: | 8.88–9.31 (m/6 H) |

Example 3

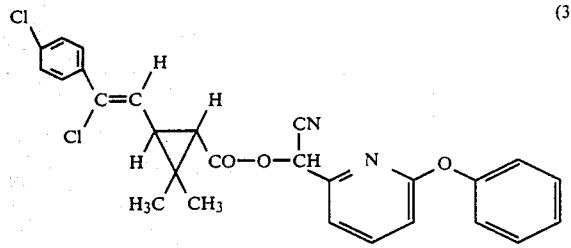     (3)

6.7 g (0.02 mol) of (±)-trans-Z-3-(2-chloro-2-(4-chloro-phenyl)-vinyl)-2,2-dimethyl-1-cyclopropanecarboxylic acid-chloride, dissolved in 10 ml of n-hexane, were added dropwise to a mixture of 40 ml of n-hexane, 1.5 g of sodium cyanide, 2 ml of water, 3.98 g (0.02 mol) of 2-formyl-6-phenoxy-pyridine and 0.5 g of tetrabutylammonium bromide at 20° to 25° C., while stirring, and the mixture was then stirred for 4 hours at 20° to 25° C. 100 ml of toluene were then added to the reaction mixture, and the latter was extracted by shaking twice with 60 ml of water. The organic phase was separated off and dried over magnesium sulphate, and the solvent was distilled off in a water jet vacuum. The last solvent residues were removed by incipient distillation for a short time at a bath temperature of 60° C./1 mm Hg. 6.4 g (77% of theory) of cyano-(6-phenoxy-2-pyridinyl)-methyl (±)-trans-Z-3-(2-chloro-2-(4-chloro-phenyl)-vinyl)-2,2-dimethyl-cyclopropanecarboxylate were obtained as a viscous yellow oil. The structure was established by the ¹H-NMR spectrum.

| ¹H—NMR in CDCl₃/TMS τ(ppm): | |
|---|---|
| vinyl-H: | 4.15 (s/1 H) |
| H<br>\|<br>—C—CN:<br>\| | 3.6–3.65 (m/1 H) |

Example 4

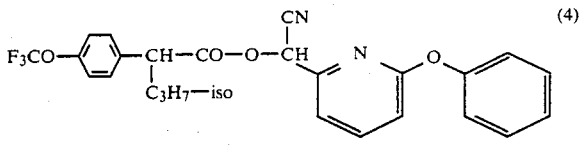     (4)

5.6 g (0.02 mol) of α-isopropyl-4-trifluoro-methoxy-phenylacetic acid-chloride, dissolved in 10 ml of n-hexane, were added dropwise to a mixture of 50 ml of n-hexane, 1.5 g of sodium cyanide, 2 ml of water, 3.98 g (0.02 mol) of 2-formyl-6-phenoxy-pyridine and 0.5 g of tetrabutylammonium bromide at 20°–25° C., while stirring, and the mixture was then stirred for 4 hours at 20° to 25° C. 100 ml of toluene were then added to the reaction mixture, and the latter was extracted by shaking twice with 60 ml of water. The organic phase was separated off and dried over magnesium sulphate, and the solvent was distilled off in a water jet vacuum. The last solvent residues were removed by incipient distillation for a short time at a bath temperature of 60° C./1 mm Hg. 7.8 g of cyano-(6-phenoxy-2-pyridinyl)-methyl α-isopropyl-4-trifluoro-methoxyphenyl-acetate were obtained as a yellow viscous oil. The structure was established by the ¹H-NMR spectrum.

| ¹H—NMR in CDCl₃/τ(ppm): | |
|---|---|
| H<br>\|<br>—C—CN:<br>\| | 3.6–3.65 (m/1 H) |

The following compounds could also be prepared analogously to Examples 1 to 4.

| Compound | |
|---|---|
| 5 | 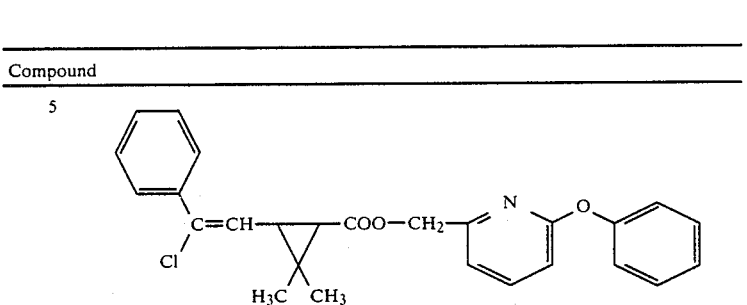 |

-continued

| Compound | |
|---|---|
| 6 | 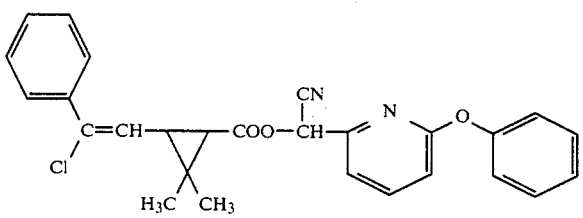 |
| 7 | 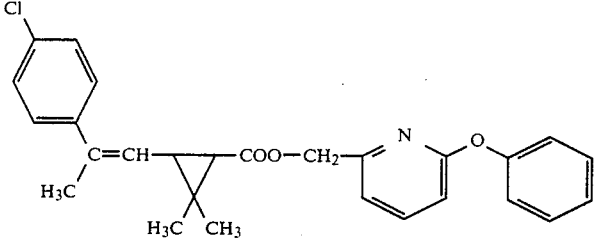 |
| 8 | 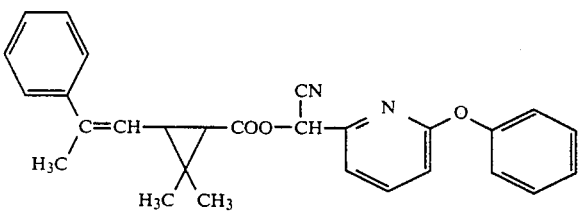 |
| 9 | 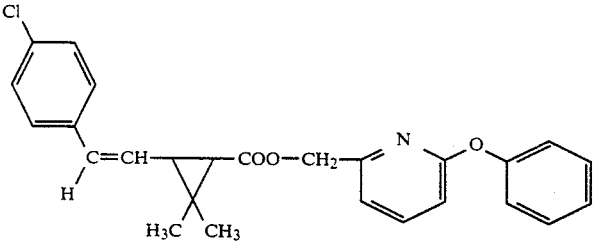 |
| 10 | 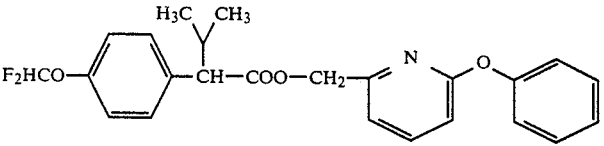 |

The pesticidal activity of the compounds of this invention is illustrated by the following examples:

Example 5

Phaedon larvae test.
Solvent: 3 parts by weight of acetone.
Emulsifier: 1 part by weight of alkylaryl polyglycol ether.

To produce a suitable preparation of active compound, 1 part by weight of active compound was mixed with the stated amount of solvent and the stated amount of emulsifier, and the concentrate was diluted with water to the desired concentration.

Cabbage leaves (Brassica oleracea) were treated by being dipped into the preparation of the active compound of the desired concentration and were infested with mustard beetle larvae (Phaedon cochleariae), as long as the leaves were still wet.

After the specified periods of time, the destruction in % was determined. 100% meant that all the beetle larvae had been killed; 0% meant that none of the beetle larvae had been killed.

In this test, for example, the following compounds showed a superior activity compared to the prior art: (1) and (2).

Example 6

Tetranychus test (resistant).
Solvent: 3 parts by weight of acetone.
Emulsifier: 1 part by weight of alkylaryl polyglycol ether.

To produce a suitable preparation of active compound, 1 part by weight of active compound was mixed with the stated amount of solvent and the stated amount of emulsifier, and the concentrate was diluted with water to the desired concentration.

Bean plants (Phaseolus vulgaris) which were heavily infested with the common spider mite or two-spotted spider mite (Tetranychus urticae) in all stages of development were treated by being dipped into the preparation of the active compound of the desired concentration.

After the specified periods of time, the destruction in % was determined. 100% meant that all the spider mites had been killed; 0% meant that none of the spider mites had been killed.

In this test, for example, the following compounds showed a superior activity compared to the prior art: (1) and (2).

Example 7

Critical concentration test/soil insects.
Test insect: Agrotis segetum larvae (in the soil).
Solvent: 3 parts by weight of acetone.
Emulsifier: 1 part by weight of alkylaryl polyglycol ether.

To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil. The concentration of the active compound in the preparation was of practically no importance, only the amount by weight of active compound per unit volume of soil, which was given in ppm (=mg/l) being decisive. The soil was filled into pots and the pots were left to stand at room temperature.

After 24 hours, the test insects were introduced into the treated soil, and after a further 2 to 7 days the degree of effectiveness of the active compound was determined in % by counting the dead and live test insects. The degree of effectiveness was 100% if all the test insects had been killed and was 0% if just as many test insects were still alive as in the case of the untreated control.

In this test, for example, the following compounds showed a superior action compared to the prior art: (1) and (2).

Example 8

Critical concentration test/soil insects.
Test insect: Phorbia antiqua grubs (in the soil).
Solvent: 3 parts by weight of acetone.
Emulsifier: 1 part by weight of alkylaryl polyglycol ether.

To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil. The concentration of the active compound in the preparation was of practically no importance, only the amount by weight of active compound per unit volume of soil, which was given in ppm (=mg/l) being decisive. The soil was filled into pots and the pots were left to stand at room temperature.

After 24 hours, the test insects were introduced into the treated soil, and after a further 2 to 7 days the degree of effectiveness of the active compound was determined in % by counting the dead and live test insects. The degree of effectiveness was 100% if all the test insects had been killed and was 0% if just as many test insects were still alive as in the case of the untreated control.

In this test, for example, the following compounds showed a superior action compared to the prior art: (1) and (2).

Example 9

Test with Boophilus microplus resistant.
Solvent: 35 parts by weight of ethylene glycol monomethyl ether; 35 parts by weight of nonylphenol polyglycol ether.

To produce a suitable preparation of active compound, three parts by weight of active compound were mixed with seven parts by weight of the solvent mixture indicated above, and the concentrate thus obtained was diluted with water to the desired concentration.

10 adult Boophilus microplus res. were immersed for 1 minute in the active compound preparation to be tested. After transfer to plastic beakers and storage in a climatically controlled chamber, the degree of destruction was determined.

In this test, for example, the following compounds showed a superior action compared to the prior art: (1) and (2).

Example 10

Test with Lucilia cuprina res. larvae.
Emulsifier: 35 parts by weight of ethylene glycol monomethyl ether;
35 parts by weight of nonylphenol polyglycol ether.

To produce a suitable preparation of active compound, three parts by weight of active compound were mixed with seven parts by weight of the abovementioned solvent mixture and the concentrate thus obtained was diluted with water to the particular desired concentration.

About 20 Lucilia cuprina res. larvae were introduced into a test tube which contained approx. 1 cm² or horse muscle and 0.5 ml of the preparation of active compound. After 24 hours, the degree of destruction was determined.

In this test, for example, the following compounds showed a superior action compared to the prior art: (1) and (2).

It will be appreciated that the instant specification and examples are set forth by way of illustration and not limitation, and that various modifications and changes may be made without departing from the spirit and scope of the present invention.

We claim:

1. A phenoxypyridylmethyl ester of the formula

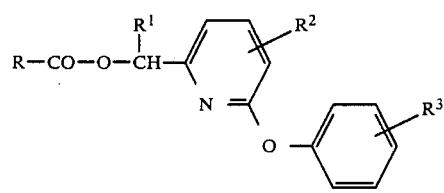

in which
R is

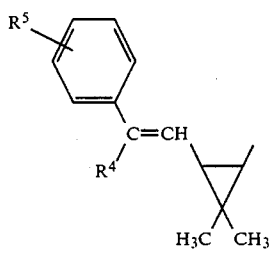

or

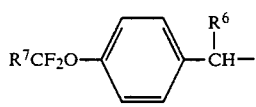

$R^1$ is a hydrogen atom, cyano, or an alkyl, alkenyl or alkinyl group containing up to 4 carbon atoms and optionally substituted by halogen, $R^2$ and $R^3$ each independently is a hydrogen or halogen atom, $R^4$ is a hydrogen, chlorine or bromine atom, a cyano group or an optionally halogen-substituted alkyl group of up to 4 carbon atoms, $R^5$ is a hydrogen or halogen atom or an optionally halogen-substituted alkyl or alkoxy group of up to 4 carbon atoms, $R^6$ is an isopropyl or cyclopropyl group, and $R^7$ is a hydrogen or fluorine atom, or a trifluoromethyl or group.

2. A compound according to claim 1, in which $R^1$ is a hydrogen atom or a cyano, methyl, ethyl, propyl, ethenyl, propenyl, ethinyl or propinyl group, $R^2$ and $R^3$ each independently is a hydrogen, fluorine, chlorine or bromine atom, $R^4$ is a hydrogen, chlorine or bromine atom, a cyano group or a $C_1$ to $C_4$ alkyl group which is optionally substituted by fluorine or chlorine, and $R^5$ is a hydrogen, chlorine or bromine atom, or an optionally fluorine and/or chlorine-substituted $C_1$ to $C_4$ alkyl or $C_1$ to $C_4$ alkoxy group.

$R^6$ is an isopropyl or cyclopropyl group, and $R^7$ is a hydrogen or fluorine atom or a trifluoromethyl or group.

3. A compound according to claim 1, in which $R^1$ is a hydrogen atom or a cyano group, $R^2$ and $R^3$ are hydrogen atoms, $R^4$ is a chlorine atom, $R^5$ is a hydrogen atom or a para-chlorine atom, $R^6$ is an isopropyl group, and $R^7$ is a fluorine atom.

4. A compound according to claim 1, wherein such compound is (6-phenoxy-2-pyridyl)-methyl 3-(2-chloro-2-(4-chlorophenyl)-vinyl)-2,2-dimethyl-1-cyclopropane carboxylate of the formula

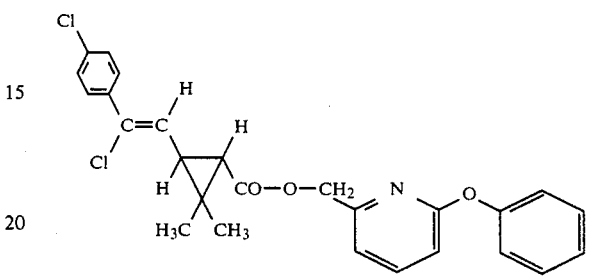

5. A compound according to claim 1, wherein such compound is (6-phenoxy-2-pyridyl)-methyl α-isopropyl-4-trifluoromethoxy-phenylacetate of the formula

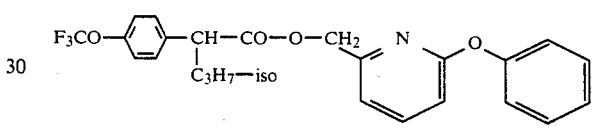

6. An insecticidal or acaricidal composition comprising (a pesticidally) an insecticidally or acaricidally effective amount of a compound according to claim 1 in admixture with a diluent.

7. A method of combating (pests) insects or acarids comprising applying to the (pests) insects or acarids, or to a habitat thereof, (a pesticidally) an insecticidally or acaricidally effective amount of a compound according to claim 1.

8. A method of freeing or protecting domesticated animals from insect-like parasites comprising applying to said animals a parasiticidally effective amount of a compound according to claim 4.

9. A method of freeing or protecting domesticated animals from insect-like parasites comprising applying to said animals a parasiticidally effective amount of a compound according to claim 5.

* * * * *

UNITED STATES PATENT AND TRADEMARK OFFICE
CERTIFICATE OF CORRECTION

PATENT NO. : 4,491,585

DATED : January 1, 1985

INVENTOR(S) : Rainer Fuchs, et al

It is certified that error appears in the above-identified patent and that said Letters Patent is hereby corrected as shown below:

| | |
|---|---|
| Col. 3, line 26 | Delete "chloride" and substitute --chlorine-- |
| Col. 5, line 67 | Delete "fo" and substitute --for-- |
| Col. 7, line 53 | Delete "olea" and substitute --oleae-- |
| Col. 17, lines 33 and 49 | Before "group" delete "or" |
| Col. 18, line 35 | Delete "(a pesticidally)" |
| Col. 18, lines 38 and 39 | Delete "(pests)" |
| Col. 18, line 40 | Delete "(a pesticidally)" |

Signed and Sealed this

Twenty-eighth Day of May 1985

[SEAL]

Attest:

DONALD J. QUIGG

Attesting Officer

Acting Commissioner of Patents and Trademarks